United States Patent [19]

Wong

[11] Patent Number: 5,165,406
[45] Date of Patent: Nov. 24, 1992

[54] ELECTROCHEMICAL SENSOR APPARATUS AND METHOD

[75] Inventor: David K. Wong, Del Mar, Calif.

[73] Assignee: Via Medical Corporation, San Diego, Calif.

[21] Appl. No.: 581,803

[22] Filed: Sep. 13, 1990

[51] Int. Cl.⁵ .............................................. A61B 5/14
[52] U.S. Cl. .................................. 128/635; 128/760; 604/4; 204/409
[58] Field of Search ............... 128/630, 632, 635, 637, 128/760; 604/4; 204/403, 411, 409

[56] References Cited

U.S. PATENT DOCUMENTS

| | | | |
|---|---|---|---|
| 3,616,409 | 10/1971 | Tosteson | 204/195 |
| 3,661,010 | 5/1972 | Neuwelt | 73/61 R |
| 3,763,850 | 10/1973 | Gaudebout et al. | 128/2 E |
| 4,340,457 | 7/1982 | Kater | 204/195 R |
| 4,450,064 | 5/1984 | Harman, III | 204/412 |
| 4,461,998 | 7/1984 | Kater | 324/438 |
| 4,492,622 | 1/1985 | Kuypers | 204/403 |
| 4,516,580 | 5/1985 | Polanyi | 128/632 |
| 4,535,786 | 8/1985 | Kater | 128/760 |
| 4,571,292 | 2/1986 | Liu et al. | 204/412 |
| 4,573,968 | 3/1986 | Parker | 604/67 |
| 4,734,184 | 3/1988 | Burleigh et al. | 204/409 |
| 4,786,394 | 11/1988 | Enzer et al. | 204/401 |
| 4,911,549 | 3/1990 | Karkar | 128/633 |
| 4,989,606 | 2/1991 | Gehrich et al. | 128/637 |

Primary Examiner—William E. Kamm
Assistant Examiner—Kevin Pontius
Attorney, Agent, or Firm—Pretty, Schroeder, Brueggemann & Clark

[57] ABSTRACT

A sensor assembly for a combination infusion fluid delivery system and blood chemistry analysis system includes a sensor assembly with each of the assembly electrodes mounted in an electrode cavity in the assembly. Each electrode cavity includes a circular ridge that defines a cylindrical inner cavity and a ring-shaped outer cavity. The circular ridge prevents the water soluble gel from wicking into the surrounding selectively-permeable membrane, and thereby provides easier manufacture, higher yield rates, and longer shelf life. A helical groove increases turbulence in the assembly, reducing the purge volume needed to flush the assembly after each sample measurement. The system includes provision for delivering the infusion fluid and measuring blood chemistry during reinfusion of the blood at approximately the same flow rates.

22 Claims, 2 Drawing Sheets

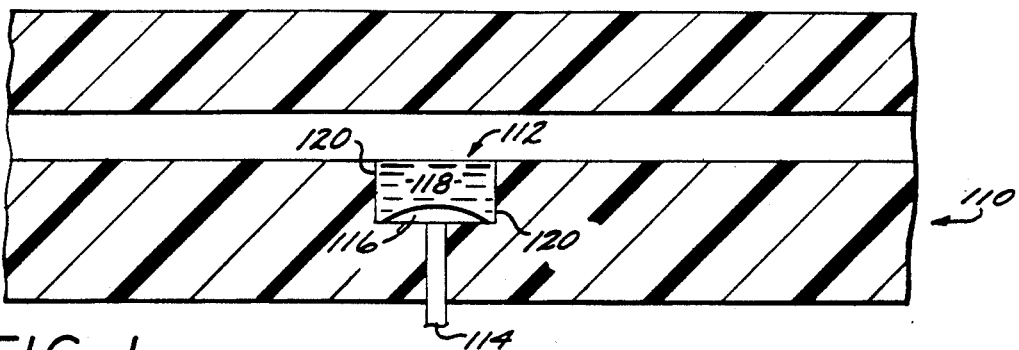
FIG. 1 PRIOR ART
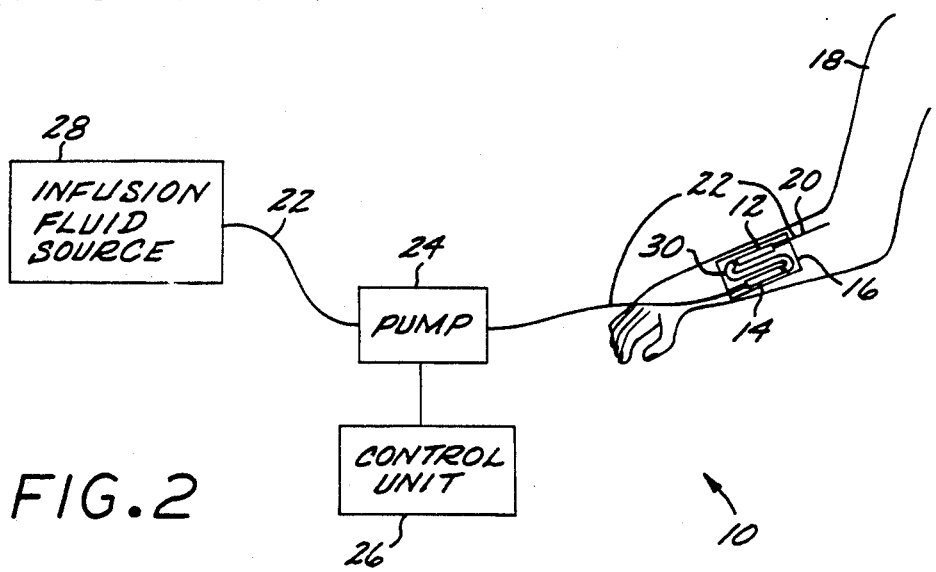
FIG. 2
FIG. 3
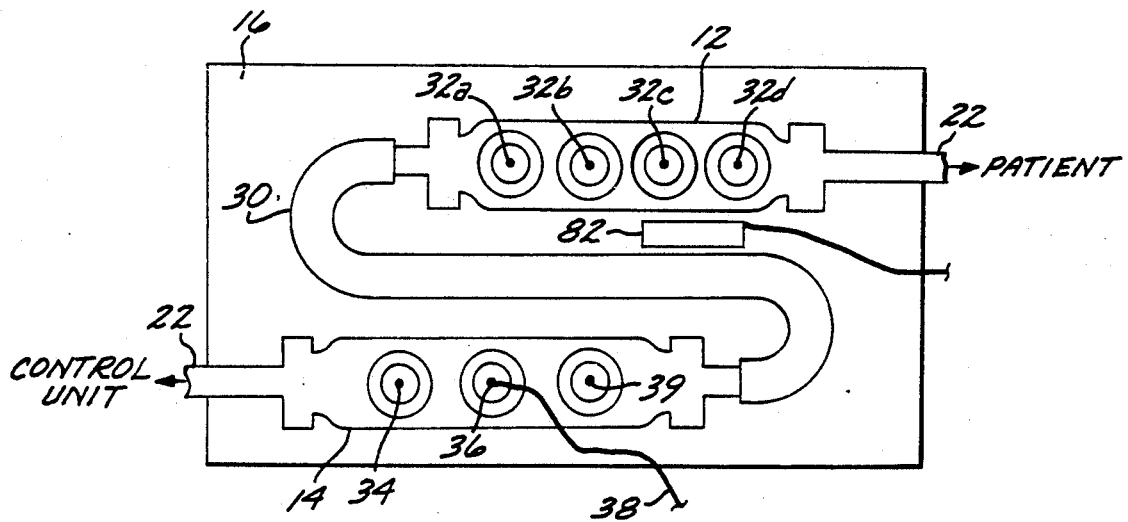

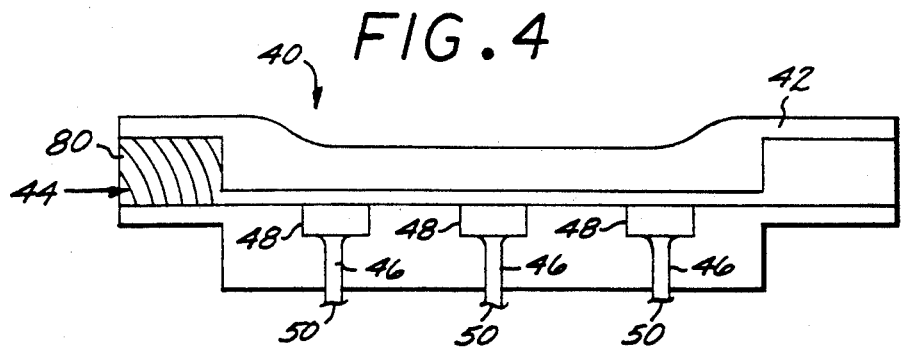
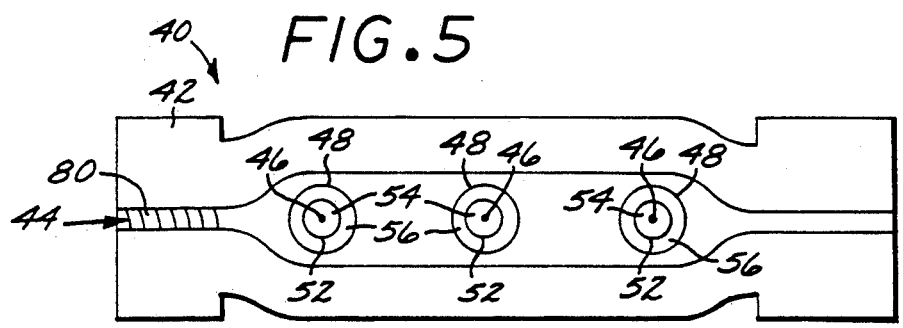
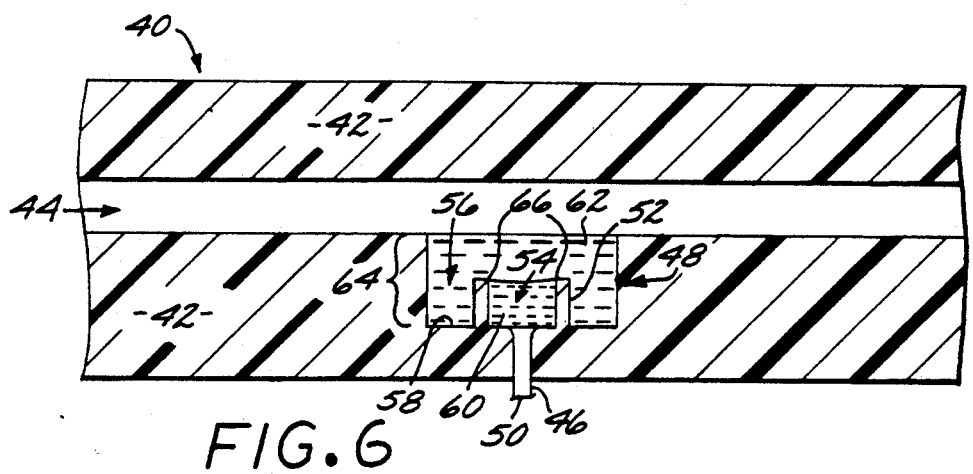
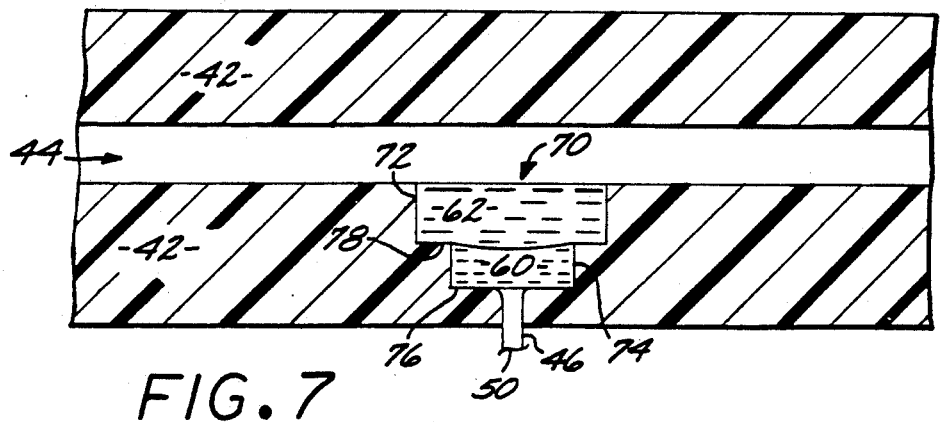

ELECTROCHEMICAL SENSOR APPARATUS AND METHOD

BACKGROUND OF THE INVENTION

1. Field of the Invention

This invention relates generally to the diagnostic testing of body fluids and, more particularly, to low-cost, disposable, ion-selective electrode assemblies for use in automated analysis systems.

2. Description of the Related Art

Electrode assemblies of this particular kind have special utility as part of infusion fluid delivery systems commonly used in hospital patient care. Such systems infuse nutrients, medications, and the like directly into the patient at a controlled rate and in precise quantities for maximum effectiveness. Infusion fluid delivery systems are connected to a patient at an intravenous (IV) port, in which a hollow needle/catheter combination is inserted into a blood vessel of the patient and thereafter an infusion fluid is introduced into the vessel at a controlled rate, typically using a peristaltic pump. Blood chemistry monitoring systems that are combined with infusion delivery systems of this kind use the IV port to periodically withdraw a blood sample, perform measurements of blood ion concentrations and the like, and then discard the blood or reinfuse it into the patient. The system then resumes delivery of the infusion fluid.

Such combined infusion fluid delivery and blood chemistry monitoring systems include an infusion line and catheter through which the infusion fluid is provided to the patient and blood samples are withdrawn. The infusion line incorporates an ion-monitoring electrode assembly having electrochemical sensors that are periodically exposed to the blood samples and thereby provide electrical signals to an analyzer for conversion into corresponding blood chemistry data. A control unit periodically halts delivery of the infusion fluid for a brief interval, during which time a blood sample is withdrawn from the patient into the infusion line and routed to the electrode assembly, which then generates the electrical signals. After the electrical signals have been received by the analyzer, the control unit disposes of the blood or reinfuses the blood sample into the patient, and the flow of infusion fluid is resumed.

The electrode assembly typically includes a reference electrode and a plurality of sensor electrodes that are each sensitive to a particular ion of interest. All of the electrodes are embedded in the base of the electrode assembly. Ion-sensitive electrodes generate electrical signals only in response to contact with the particular ion to which they are sensitive, and therefore provide selective measurement of the amount of that ion in the blood. Sensor electrodes can be provided to measure, for example, blood calcium, hydrogen ion, chloride, potassium, and sodium. In a differential measurement system, the reference electrode might be a pseudo-reference electrode (e.g., a chloride or sodium electrode) that is continuously exposed to a calibration or reference fluid. Alternatively, in a non-differential measurement system, the reference electrode can be exposed either to the reference fluid or to the blood while maintaining its fixed rest or steady-state potential.

In a differential measurement system, during the delivery of calibration fluid, the calibration fluid flows past both the reference electrode and the sensor electrodes, and the electrical potential between the reference electrode and each sensor electrode is measured. This provides a calibration measurement of the electrode assembly. During a subsequent blood chemistry measurement, a blood sample is drawn into the electrode assembly, where it comes into contact with the sensor electrodes, but not the reference electrode. The electrical potential between the reference electrode and each sensor electrode is measured again and compared with the earlier calibration measurement to provide an indication of the ion concentration in the blood of the particular ion to which the sensor electrode is sensitive. After measurement is completed, the blood sample is discarded or reinfused from the electrode assembly back into the patient, and delivery of infusion fluid is resumed.

The accuracy of measurement described above can be adversely affected by blood cells and other blood components (e.g., protein) that build up in the various spaces and crevices of the sensor assembly. That is, the accumulation of extraneous blood cells around the sensor electrodes can result in erroneous calibration and inaccurate measurement of blood chemistry. To avoid this problem, successive measurements generally cannot be taken unless the electrode assembly has been thoroughly purged of blood cells between measurements. Thus, a specified purge volume of infusion or calibration fluid must be passed through the electrode assembly after each measurement.

To reduce the blood fouling problem described above, it is known to provide a smooth flow path in the electrode assembly. Some assemblies, for example, provide flush-mounted electrodes, in which the electrodes are located in a sensor cavity and a water soluble reference material or gel is placed above the electrode and a polymer-based, selectively-permeable material is placed on top of the gel to form a smooth flow pathway for samples. The selectively-permeable material presents a smooth outer surface to the fluid flow, flush with the electrode housing, and it allows only selected ions to reach the reference gel and thereby produce a reading from the electrode.

Such flush-mounted electrode designs, however, can be difficult to manufacture. To provide accurate readings, a precise separation must be provided between aqueous-based internal reference gel and the polymer-based selectively permeable material, and the electrode must be kept free of any contact with the fluid being measured. For example, in the prior art electrode assembly illustrated in FIG. 1, a housing 110 having a cavity 112 with an electrode 114 is capped by a dry bead of reference gel material 116 and covered by a selectively-permeable membrane layer 118. The gel is a water-permeable material that can creep up the side walls 120 of the cavity. This is commonly referred to as wicking, and it can result in inaccurate measurement of blood chemistry. Accurate measurement of blood chemistry requires precise layer thickness of the membrane layer 118 and a good bond between that layer and the housing cavity 112. In the assembly of FIG. 1, wicking allows the reference gel material 116 to spread to areas of the cavity where the selectively-permeable layer 118 will be deposited. This weakens the bond between the housing and the selectively-permeable layer, and it can allow the layer to lift up and out of the cavity or allow the fluid being measured to travel along the cavity wall and reach the electrode, shorting the electrode out. Therefore, wicking also reduces the electrode assembly's shelf life.

Other factors besides the accumulation of blood cells around the electrode in the fluid path can also adversely affect the accuracy of the measurement. For example, the flow rate of the blood can influence the collection of blood cells or the reaction of the electrode during measurement. Instability in the rate of blood sample flow might influence the travel of ions to the electrode and induce inaccurate readings. In addition, patient comfort and ease of assembly replacement are important considerations in the selection of competing electrode assembly configurations. Conventional assemblies can be rather unwieldy, making them uncomfortable for patients and inconvenient for medical personnel in changing assemblies after use.

From the discussion above, it should be apparent that there is a need for an ion-monitoring electrode assembly useful, for example, in a combined infusion fluid delivery and blood chemistry measurement system that provides accurate, reliable measurements of blood chemistry, that avoids collection of blood cells in the assembly pathway, and that provides an increased shelf life and production yield, along with greater patient comfort and ease of use. The present invention satisfies this need.

SUMMARY OF THE INVENTION

The present invention is embodied in an ion-monitoring electrode assembly suitable for use in a combined infusion fluid delivery and blood chemistry measurement system, the electrode assembly including an electrode cavity with a barrier structure in the cavity bottom floor to contain the reference gel material and prevent wicking, while the upstream sensor conduit of the assembly includes an internal turbulence structure. By confining the gel, the barrier structure gives more precise deposition and separation of layers, increasing the yield from manufacturing the electrode assemblies and providing a longer shelf life. The conduit turbulence structure adds turbulence to the flow of infusion or calibration fluid into the electrode assembly, providing an agitating flow through the assembly that helps dislodge any blood cells collected around the electrodes, as well as other parts of the assembly. This reduces the collection of blood cells, increases the measurement accuracy, and reduces the purge volume necessary for accurate measurement, thereby reducing the time interval between successive measurements.

The control system for the assembly advantageously controls the flow of fluids such that the infusion fluid is used for calibration and is made to flow through the electrode assembly during calibration at a predetermined flow rate. Each time the blood is drawn up into the infusion line, it is then made to flow past the sensor electrode during measurement at substantially the same predetermined flow rate as during calibration. This eliminates any effect the fluid flow rate might otherwise have on the measurements. Further, the electrode assembly can be used for both a reference assembly having a reference electrode and a sensor assembly having one or more sensor electrodes, with the reference assembly and sensor assembly mounted side-by-side in a compact unit that is easy to remove and replace.

The electrodes in the electrode assembly are mounted in a cavity located in the base of the assembly. The barrier structure advantageously comprises a circular stepped cavity, or cup, in the electrode cavity floor surrounding each electrode and having a sharp top corner. The volume within each circular cup and around each electrode is substantially filled with a water-soluble reference gel for the particular ion of interest, and the remainder of the electrode cavity is filled with a polymer-based, selectively-permeable material, or ion-selective membrane. The membrane presents a smooth surface to the fluid flow, so as to minimize the collection of blood cells around the site of the electrodes. Alternatively, the barrier structure can comprise a circular ridge, or wall, extending upwardly from the electrode cavity floor and surrounding each electrode, defining a cup or bowl having a sharp inner rim. The volume within the cup is substantially filled with the reference gel.

The turbulence structure advantageously comprises a helical groove formed in the assembly housing, upstream of the sensor electrodes and in the fluid flow path. This creates turbulence in the flow of fluid through the electrode assembly, which promotes dislodging of any blood cells collected around the electrodes, without appreciably increasing turbulence between the blood and infusion fluid upstream of the electrode assembly when a sample is being taken.

The control system in accordance with the present invention calibrates during infusion and takes measurements of blood chemistry during the time that sample blood drawn into the infusion line is being reinfused into the patient. That is, substantially the same flow rates are used in the infusion line through the electrode assembly when infusion fluid flows during calibration and also when blood flows during measurement. More particularly, the control system controls the infusion pump of the combined infusion fluid delivery and blood chemistry measurement system such that the infusion fluid is pumped past the reference and sensor electrodes at a fixed flow rate during calibration, and the blood maesurement is taken while the blood is infused back into the patient at approximately the same flow rate.

The reference electrode and sensor electrodes can be provided in separate assemblies for a blood chemistry measurement system, placed side-by-side in a compact unit. Placing the reference and sensor assemblies in a single unit provides an assembly that is more comfortable for the patient, facilitates removal and replacement of the assemblies, and also allows more i precise calibration of the blood volume withdrawn and fluid infused, providing increased accuracy and reliability. For example, the time needed for the desired amount of blood to be withdrawn into the sensor assembly can be calculated and an error condition can be signalled if this time is exceeded with no indication of blood in the assembly. The diameter of the infusion line between the assemblies can be enlarged, reducing the electrical resistance of the fluid between the assemblies and providing more accurate readings.

A temperature sensing electrode can be provided with the sensor electrodes, to provide a temperature signal that can be used to correct the sensed readings to compensate for changes in temperature. Furthermore, an additional electrode can be provided to act as a key to the controller to signal what particular types of sensors are provided in the assembly. For example, standardized groupings of sensors can be provided, and the keying electrode can cause the controller to act appropriately for the group of sensors provided.

Other features and advantages of the present invention should be apparent from the following description of the preferred embodiment, which illustrates, by way of example, the principles of the invention.

BRIEF DESCRIPTION OF THE DRAWINGS

FIG. 1 is a cross-sectional view of a prior art electrode assembly.

FIG. 2 is a schematic diagram of a combination infusion fluid delivery and blood chemistry analysis system in accordance with the present invention.

FIG. 3 is a plan view of a reference/sensor electrode assembly in accordance with the present invention.

FIG. 4 is a cross-sectional view of an electrode assembly in accordance with the present invention.

FIG. 5 is a plan view of the electrode assembly illustrated in FIG. 4.

FIG. 6 is an enlarged cross-sectional view showing details of one sensor electrode in the electrode assembly of FIG. 4.

FIG. 7 is an enlarged cross-sectional view showing details of an alternate configuration of one sensor electrode for use in the electrode assembly of FIG. 4.

DESCRIPTION OF THE PREFERRED EMBODIMENTS

The following description of the preferred embodiments of the invention is not to be taken in a limiting sense, but is made merely for the purpose of illustrating the general principles of the invention. The following detailed description is of the best presently contemplated mode of carrying out the present invention.

The combination infusion fluid delivery system and blood chemistry analysis system 10 of FIG. 2 includes a sensor assembly 12 and a reference assembly 14 having electrodes constructed in accordance with the present invention, the two assemblies being mounted side-by-side on an arm board 16 that is attached to a patient 18. While the assembly includes a separate sensor assembly and reference assembly, and therefore is suited to a differential measurement system, it is to be understood that the assemblies could be integrated into a single unit to operate in a non-differential measurement system. The sensor assembly 12 is connected to the patient via an intravenous (IV) port 20 and an infusion line 22, which continues upstream of the sensor assembly to the reference assembly 14 and then to a peristaltic pump 24 that is controlled by a control unit 26. Those skilled in the art will appreciate that the pump and control unit can alternatively be integrated into a single unit. Finally, the infusion line 22 continues upstream of the pump to an infusion fluid source 28.

During a calibration mode of the system 10, the control unit 26 controls the pump 24 and meters infusion fluid from the infusion fluid source 28, through the pump, past the reference assembly 14, past the sensor assembly 12, and into the patient 18. The reference and sensor assemblies include electrodes constructed in accordance with the present invention, and during the calibration mode the electrical potential between respective electrodes of the two assemblies is measured to provide a series of calibration measurements for the system 10.

During a measurement mode of the system, blood is withdrawn from the patient 18 into the infusion line 22 past the sensor assembly 12 but not up to the reference assembly 14, as described further below, and the electrical potential between respective electrodes is again measured. The electrical potential will be changed from the calibration measurements, and the difference corresponds to a calculated amount of a particular ion in the patient's blood. The sensor assembly 12 can include, for example, electrodes that are sensitive to blood chemistry ions including calcium, hydrogen, chloride, potassium, and sodium.

As shown in FIG. 3, the sensor electrode assembly 12 and the reference electrode assembly 14 contain electrodes that are constructed in accordance with the present invention. The assemblies are in flow communication via a connecting conduit 30 in the infusion line 22. The sensors in the sensor assembly have sensing electrodes 32a, 32b, 32c, and 32d that each react to a fluid in the assembly and generate a voltage signal relative to the reference assembly 14. One of the reference assembly's electrodes 34 is used as patient or solution ground, and are connected to what is known as an isolated ground (not illustrated). A second reference electrode 36 is a common reference for the sensor electrodes. That is, the sensor electrode electrical signals are with respect to the common reference, thereby providing differential measurement.

A temperature sensing line 38 is provided from the reference electrode 34 to the control unit 26. The temperature sensing line provides the control unit with a signal that represents the temperature of the calibration fluid. This information is used to calibrate the output signals from the electrodes to give more accurate blood chemistry readings. Finally, a third electrode 39 has a resistance value that is keyed to the particular group of sensor electrodes 32 being used on the board 16. In this way, the system control unit can be informed of the particular sensors in use and can act accordingly.

The electrode assemblies 12 and 14 will now be discussed in greater detail. An electrode assembly 40 in accordance with the present invention, shown in FIGS. 4 and 5, includes an assembly housing 42 or substrate with a fluid pathway 44. Three electrodes 46 are shown embedded in the housing, each in a separate electrode cavity 48 immediately adjacent to the fluid pathway. The free ends 50 of each electrode are connected to the control unit 26 for further signal processing. Each electrode cavity includes a barrier structure in the form of a circular ridge 52 encircling each electrode, defining a generally cylindrical, inner gel cavity 54 and a generally ring-shaped outer cavity 56.

A detailed cross-sectional view of an electrode provided in FIG. 6 shows that the circular ridge 52 extends upwardly from the floor 58 of the electrode cavity 48. The inner cavity 54 formed by the circular ridge 52 in the electrode cavity 48 is filled with a water soluble material, or internal reference gel 60. The outer cavity 56 is filled with an ion-selective material 62, which also fills the remainder of the electrode cavity up to a level that is flush with the fluid pathway 44 in the sensor housing 42, thereby creating a selectively permeable membrane 64 that is in contact with the fluid pathway. The top of the circular ridge has a sharp inner corner 66 that prevents the gel from creeping over the ridge into the housing substrate 42 where the ion-selective material 62 will be deposited. That is, the sharp top inner corner of the circular ridge prevents wicking of the gel. This increases the yield from the manufacturing process, because the surface of the housing 58 is kept free of the gel, thus providing a better bond with the ion-selective material. The housing 42 defining the electrode cavity comprises a substrate for various materials surrounding the electrode, as will be described below.

The selectively-permeable membrane 64 allows particular ions to change the electrical potential at the electrode 46, and also keeps aqueous fluids in the blood away from the gel 60 and electrode that would otherwise short out the electrode and provide erroneous measurements. In the preferred embodiments, the electrode cavity 48 has a diameter of approximately 0.150 inches and is approximately 0.020 inches deep, while the circular ridge 52 has an inner diameter of approximately 0.100 inches and a height of approximately 0.008 inches. The thickness of the selectively-permeable membrane 64 is preferably greater than approximately 0.003 inches. It is to be understood, however, that such dimensions are exemplary only.

In constructing the electrode assembly 40, it is important for the ion-selective material 62 to be securely bonded to the housing 42, or sensor substrate. If the bond between the ion-selective material and the housing is not secure, water in the fluid pathway 44 can penetrate between the material and the housing, and can find its way to the gel 60. When this happens, an ionically conductive path is formed between the blood sample and the sensor electrode 46, effectively shorting out the electrode and giving a false measurement.

The quality of the bond between the housing 42 and the ion-selective material 62 depends in part on the surface cleanliness of the housing. If any gel 60 is deposited on the housing where the ion-selective material is to be placed, the gel will degrade the bond between the housing and the material over time to the point where the material will not remain bonded. When this occurs, substantially the entire mass of ion-selective material can spontaneously lift out of the electrode cavity 48, whereupon the assembly is useless. Furthermore, a poor bond increases the likelihood of forming an ionically conductive path that can reach the electrode 46 and short it out. Therefore, when the gel is placed in the electrode cavity, it should be kept completely out of contact with the housing 42 except in the precise areas in which it is desired.

The circular ridge 52 helps keep the gel 60 away from the housing 42 in the areas where the ion-selective material 62 will be deposited. This increases the quality of the bond between the material and the housing, and therefore improves the electrode assembly's shelf life. It also increases the manufacturing yield, because a greater proportion of the assemblies can pass initial quality screening tests.

A drop of the water soluble reference gel 60 is deposited in the inner gel cavity 54 to a level approximately even with the top of the circular ridge 52 and is allowed to dry. The sharp inner corner 66 helps prevent wicking of the gel into the ion-selective material 62. Because the surface of the cavity 58 is kept free of the gel, a better bond with the ion-selective material is provided, thereby increasing the yield from the manufacturing process.

With the reduction in wicking, a larger proportion of the electrode assemblies produced will meet measurement tolerances, increasing yield. Further, the circular ridge 52 creates a longer pathway for water to travel to reach the gel 60 and electrode 46, should the water in the fluid path 44 happen to penetrate between the ion-selective material 62 and the housing 42. This is most apparent when comparing FIG. 1 with FIG. 6. Thus, the longer water vapor pathway of the FIG. 6 structure further increases the yield, and also increases the assembly's shelf life, up to approximately one year, unlike previous assemblies, which typically have much shorter shelf lives. Finally, the circular ridge, by confining the gel 60 to a particular cavity 54, makes it easier to obtain a selectively permeable membrane 64 of the desired thickness, further increasing the yield and extending the assembly's shelf life.

The detailed cross-sectional view of a sensor electrode in FIG. 7 shows an alternate configuration in accordance with the present invention. The FIG. 7 configuration is somewhat easier to manufacture, as compared with the FIG. 6 configuration. In the FIG. 7 configuration, an electrode cavity 70 is formed in a housing 42 by a vertical wall 72 having a first diameter and a first depth, a second vertical wall 74 having a second diameter less than the first and a second depth, and a substantially flat floor 76. An electrode 46 extends into the housing 42 through the cavity floor, and is then covered with the aqueous-based internal reference gel 60. A ledge 78 connects the bottom of the first vertical wall and the top of the second vertical wall, and meets the second vertical wall at an angle of approximately 90° so as to form a sharp corner.

The sharp corner formed by the ledge 78 and the second vertical wall 74 provides the benefits of the previously described configuration of FIG. 6, in that the sharp corner prevents wicking of the gel and helps keep the gel away from the housing 42 in the areas where the ion-selective material 62 will be deposited. This increases the quality of the bond between the material and the housing, thereby improving the shelf life of the electrode assembly. Comparison with FIG. 1 shows the increased path that ions must travel to reach the electrode 46. It should be appreciated that any ionically-conductive pathway formed due to failure of the bond between the ion selective material and the housing would have an even greater distance to travel in the FIG. 6 configuration as compared to the FIG. 7 configuration. In fact, the FIG. 6 configuration has been found to provide somewhat better results than the FIG. 7 configuration. Nevertheless, both present an improvement over conventional electrode assemblies.

The combination infusion fluid delivery system and blood chemistry analysis system of FIG. 2 referred to previously includes the sensor electrode assembly 12 having various electrodes sensitive to particular blood chemistry ions, such as calcium, hydrogen, chloride, potassium, and sodium, and is constructed in accordance / with the assembly illustrated in FIGS. 4–6. As shown in FIGS. 2 and 3, the sensor assembly 12 and reference assembly 14 are in flow communication, separated by a connecting loop 30 of the infusion line 22 that is approximately four to six inches in length. The connecting loop advantageously has a larger internal diameter than the remainder of the infusion line 22. The larger diameter facilitates cleaning the line of bubbles and reduces the electrical resistance of the fluid between the electrodes. The reduced resistance increases the accuracy of measurement.

A helical groove 80 in the fluid pathway 44 upstream of the electrodes, shown best in FIGS. 4 and 5, creates turbulence in the downstream flow of infusion fluid through the sensor assembly 12, which helps dislodge any blood cells that might otherwise collect around the site of the electrodes. The housing 42 is constructed of a generally non-porous material, such as plastic, and therefore the helical groove can conveniently be formed using conventional injection molding techniques. The turbulent flow of infusion fluid quickly flushes the sensor assembly of any remaining blood cells, reducing the purge volume of infusion fluid necessary before calibration and measurement can again resume. By being located only at the upstream end of the sensor assembly, the helical groove minimizes mixing of infusion fluid and blood while the blood sample is drawn from the body, but maximizes flushing of blood from the sensor assembly during reinfusion of the blood.

During the measurement mode of operation, the delivery of infusion fluid from the infusion fluid source 28 into the patient is halted. The direction of flow of the infusion fluid in the line 22 is then reversed. That is, infusion fluid in the line is pumped back into the fluid source. This process eventually withdraws blood from the patient into the infusion line 22 past the sensor assembly 12 and into the connecting loop 30, but not far enough to reach the level of the reference assembly 14. This is a volume of approximately 0.5 cc of blood.

An optical sensor 82 is provided on the armboard 16 to detect the presence of blood in the sensor assembly 12 upstream of the first sensor electrode 32d. The optical sensor, for example, distinguishes between the clear infusion fluid and the dark, reflective blood. After the withdrawal of blood from the patient 18 and into the line 22 is begun, approximately 2-3 seconds should elapse before blood appears adjacent the sensor 82. If no blood is detected in this time interval, the control unit 26 generates an error signal to alert the operator of a problem. This timing feature can be used to adjust the volume of blood withdrawn, as withdrawal can be set to end at a predetermined time relative to the detection of blood in the sensor assembly.

After the blood is drawn into the line 22, it remains in place for approximately 15 to 20 seconds while the system stabilizes. During this period, the blood in the infusion line is reinfused into the patient 18 under control of the control unit 26 at approximately the same rate as that at which the infusion fluid was earlier delivered into the patient during calibration. After a short time interval of reinfusion, for stabilization of the sensors, the potential differences between the respective electrodes of the reference assembly 14 and sensor assembly 12 are measured and provided to the control unit 26. Making the blood chemistry measurements at a blood flow rate equal to that of the earlier calibrating flow rate eliminates any effect on the measurements that the fluid flow might otherwise have. This yields an accurate reading of the blood chemistry parameters.

The temperature sensing line 38 from the second reference electrode 36 provides the control unit 26 with an indication of the calibration fluid temperature. The measured electrical potential from the various electrodes will change with the calibration fluid temperature such that temperature changes in the calibration fluid from the time of calibration to the time of measurement can provide inaccurate ion concentration data. Therefore, the control unit can use the temperature information to adjust the blood chemistry readings to compensate for the changes in temperature, providing increased accuracy and reliability.

Eventually, after the blood chemistry measurements have been completed and the blood sample has been reinfused into the patient 18, additional infusion fluid drawn from the fluid source 28 proceeds through both the infusion line 22 and sensor assembly 12 and back into the patient. The control unit 26 continues the flow of infusion fluid until a purge volume of fluid, roughly eight to ten times that of the drawn blood, has passed through the sensor assembly. This takes approximately two minutes. Thus, the control unit allows measurements to be taken at approximately two minute intervals. If the optical sensor 82 detects blood in the sensor assembly 12 after the purge volume has been passed, the control unit 26 generates an error signal to alert the operator of a problem.

It should be appreciated that the present invention provides an improved electrode assembly that has a smooth pathway for the flow of infusion fluid and sample material, such as blood. The electrode assembly includes electrodes embedded in the assembly in an electrode cavity. Each electrode cavity includes a barrier structure surrounding the electrode and dividing the electrode cavity into a central gel cavity and an outer ion-selective material cavity. The barrier structure provides for more positive separation between the water soluble gel and the ion-selective material. This increases the accuracy of measurements, reduces the difficulty of manufacturing, increases the manufacturing yield, and increases the shelf life of the assemblies. A helical groove turbulence structure in the upstream end of the fluid pathway increases turbulence in the flow of infusion fluid after measurement, flushing from the assembly substantially all remaining blood material with a reduced purge volume and ensuring more accurate calibration. The control unit of a combined infusion fluid delivery and blood chemistry analysis system in accordance with the present invention ensures that the fluid flow rate through the sensor assembly is approximately the same during calibration and during measurement. This eliminates the effect of fluid flow and turbulence on the measurements. A reference assembly containing at least one reference electrode and a sensor assembly having an electrode for each ion of interest can be mounted adjacent one another in a compact unit that increases patient comfort and makes removal and replacement easier.

While the present invention has been described with respect to a preferred embodiment, it is to be understood that variations may occur to those skilled in the art. The configuration of the electrode cavity and barrier structure, for example, can be varied without departing from the teachings of the present invention. The pumping rate of the control unit, for example, may also be varied from that disclosed without departing from the teachings of the present invention, and a non-differential measurement can be used. The invention, therefore, should not be seen as limited to the particular apparatus and method described herein, but it should be understood that the present invention has wide applicability with respect to ion selective electrodes and fluid analysis systems of different configurations. Such alternate configurations can be achieved by those skilled in the art in view of the description herein.

I claim:

1. An electrochemical electrode assembly for measuring the characteristics of a fluid flowing through the assembly, the assembly having a housing with a fluid flow pathway and with at least one electrode cavity in the housing located adjacent to the fluid flow pathway, and at least one electrode embedded in a bottom wall of the electrode cavity, the assembly further comprising:

separation means for dividing the electrode cavity into two sub-cavities comprising a selectively-permeable material portion and a reference material portion that is contained within the selectively-permeable material portion, and for defining a sharp corner in the electrode cavity between the two portions;

an internal reference material deposited in the reference material portion; and an ion-selective material deposited in the selectively-permeable material portion.

2. An electrode assembly as recited in claim 1, further comprising turbulence means located upstream of the electrode cavity for generating turbulence in the fluid flow through the fluid flow channel of the assembly.

3. An electrode assembly as recited in claim 2, wherein the turbulence means comprises a helical groove in the portion of the housing that defines the fluid flow pathway.

4. An electrode assembly as recited in claim 1, wherein the separation means comprises a circular ridge projecting upwardly from the bottom wall of the electrode cavity, defining the selectively-permeable material portion as an outer ring-shaped recess and defining the reference material portion as a centrally-located, generally cylindrical recess.

5. An electrochemical electrode assembly for measuring the characteristics of a fluid flowing through the assembly, the assembly having a base with a fluid flow channel and with at least one electrode cavity located adjacent to the channel and at least one electrode embedded in the bottom wall of the electrode cavity, the assembly further comprising:

a circular ridge projecting upwardly rom the bottom wall of the electrode cavity, dividing the electrode cavity into an outer ring-shaped recess and a centrally-located generally cylindrical recess, the circular ridge having a sharp corner at its top edge encircling the cylindrical recess;

an internal reference material deposited into the cylindrical recess so as to cover the top of the embedded electrode; and a selectively-permeable material filling the remainder of the electrode cavity.

6. An electrochemical electrode assembly for connection in the path of a fluid flow line and for measuring the characteristics of a fluid flowing through the flow line, comprising:

an elongated reference assembly having at least one reference electrode;

an elongated sensor assembly having at least one sensor electrode sensitive to a predetermined ion;

a connecting flow line carrying the fluid to be measured between the reference assembly and sensor assembly;

wherein the reference assembly and sensor assembly are mounted in side-by-side relationship;

control means for regulating the flow of the fluid through the assembly; and fluid sensing means for sensing the presence of the fluid in the connecting flow line and providing this information to the control means;

wherein the control means determines when the fluid should be present in the sensor assembly for proper operation and provides an error signal when proper operation is not indicated.

7. An electrochemical electrode assembly as recited in claim 6, wherein the connecting flow line has a length of approximately 4 to 6 inches.

8. An electrochemical electrode assembly as recited in claim 6, wherein the inside diameter of the connected flow line is greater than the inside diameter of the flow line.

9. An electrochemical electrode assembly for connection in the path of a fluid flow line and for measuring the characteristics of a fluid flowing through the flow line comprising:

an elongated reference assembly having at least one reference electrode;

an elongated sensor assembly having at least one sensor electrode sensitive to a predetermined ion; and a connecting flow line carrying the fluid to be measured between the reference assembly and sensor assembly;

wherein the reference assembly and sensor assembly are mounted in side-by-side relationship;

and wherein either the reference assembly or sensor assembly, or both, includes a base with at least one electrode cavity having an electrode embedded in a bottom wall of the cavity, and separation means for dividing the electrode cavity into two sub-cavities comprising a selectively-permeable material portion and a reference material portion that is contained the selectively-permeable material portion, and for defining a sharp corner in the electrode cavity between the two portions.

10. An electrochemical electrode assembly as recited in claim 9, further comprising turbulence means upstream of the electrode cavity for generating turbulence in the fluid flow through the assembly.

11. An electrochemical electrode assembly as recited in claim 10, wherein the turbulence means comprises helical grooves in the reference assembly and the sensor assembly.

12. An electrochemical electrode assembly as recited in claim 9, wherein the separation means comprises a circular ridge projecting upwardly from the bottom wall of the electrode cavity, defining the selectively-permeable material portion as an outer ring-shaped recess and defining the reference material portion as a centrally-located, generally cylindrical recess.

13. A method of computing a predetermined ion level in a test material from a patient, the method comprising the steps of:

providing a sensor assembly having a fluid flow pathway for flow of the test material, the fluid flow pathway having an upstream end and a downstream end that is in communication with the patient, the sensor assembly having a reference electrode and sensor electrodes mounted in the assembly in communication with the flow of the test material, the reference electrode being upstream of the sensor electrodes;

providing a calibration fluid communicating with the sensor assembly at the upstream end;

controlling the flow of the calibration fluid into the sensor assembly during a calibration mode at a predetermined calibration flow rate;

halting the flow of the calibration fluid to begin a measurement mode;

drawing a sample of test material from the patient into the sensor assembly up to, but not reaching, the reference electrode; and controlling the flow of the test material through the sensor assembly past the sensor electrode back into the patient so as to have a fluid flow rate approximately equal to the calibration flow rate during the calibration mode.

14. A method as recited in claim 13, wherein the calibration fluid is an infusion fluid that is infused into the patient during the calibration mode.

15. An electrochemical sensor apparatus for a combined infusion fluid delivery and blood chemistry monitoring system for measuring the characteristics of a patient's blood during a measurement mode and for calibrating the measurement during a calibration mode, the apparatus comprising:
- a sensor electrode assembly having a base with at least one electrode cavity and at least one sensor electrode embedded in a bottom wall of the electrode cavity;
- a pump in flow communication with the patient's blood and the infusion; and
- a controlling means for regulating the pump so as to control the flow of the infusion fluid into the patient and the withdrawal of the blood from the patient and the reinfusion of the blood back into the patient such that infusion fluid flows into the patient during the calibration mode and blood flows into the patient during the measurement mode;
- wherein the controlling means regulates the flow of infusion fluid during the calibration mode and regulates the flow of blood during the measurement mode to be at substantially equal flow rates.

16. An electrochemical sensor apparatus as recited in claim 15, further including a reference assembly having at least one reference electrode substantially identical to the sensor electrode, mounted in the fluid flow of the apparatus, upstream of the sensor assembly.

17. An electrochemical sensor apparatus as recited in claim 16, wherein the controlling means further regulates the pump during the measurement mode such that the pump draws blood into the apparatus past the sensor assembly but stops it short of the reference assembly.

18. An electrochemical sensor apparatus as recited in claim 16, wherein the sensor assembly includes turbulence means upstream of the electrode cavity for generating turbulence in the fluid flow through the assembly.

19. An electrochemical sensor apparatus as recited in claim 18, wherein the turbulence means comprises helical grooves in the sensor electrode assembly and the reference assembly.

20. An electrochemical sensor apparatus for a combined infusion fluid delivery and blood chemistry monitoring system for measuring the characteristics of a patient's blood during a measurement mode and for calibrating the measurement during a calibration mode, the apparatus comprising:
- a sensor electrode assembly having a base with at least one electrode cavity and at least one sensor electrode embedded in a bottom wall of the electrode cavity;
- a pump in flow communication with the patient's blood and the infusion fluid; and
- a controller that regulates the pump so as to control the flow of the infusion fluid into the patient and the withdrawal of the blood from the patient and the reinfusion of the blood back into the patient such that infusion fluid flows into the patient during the calibration mode and blood flows into the patient during the measurement mode, wherein the controller regulates the flow of infusion fluid during the calibration mode and regulates the flow of blood during the measurement mode to be at substantially equal flow rates;
- a reference assembly having at least one reference electrode, substantially identical to the sensor electrode, mounted in the fluid flow of the apparatus, upstream of the sensor assembly; and
- a length of conduit extending between the sensor assembly and the reference assembly, wherein the sensor assembly and reference assembly are mounted adjacent each other and the conduit between them is formed into a loop.

21. An electrochemical sensor apparatus as recited in claim 20, wherein the loop is approximately from 4 to 6 inches in length.

22. An electrochemical sensor apparatus for a combined infusion fluid delivery and blood chemistry monitoring system for measuring the characteristics of a patient's blood during a measurement mode and for calibrating the measurement during a calibration mode, the apparatus comprising:
- a sensor electrode assembly having a base with at least one electrode cavity and at least one sensor electrode embedded in a bottom wall of the electrode cavity;
- a pump in flow communication with the patient's blood and the infusion fluid;
- a controller that regulates the pump so as to control the flow of the infusion fluid into the patient and the withdrawal of the blood from the patient such that infusion fluid flows into the patient during the calibration mode and blood is withdrawn from the patient during the measurement mode, wherein the controller regulates the flow of infusion fluid during a calibration mode and regulates the flow of blood during a measurement mode to be at substantially equal flow rates; and
- a reference assembly having at least one reference electrode, substantially identical to the sensor electrode, mounted in the fluid flow of the apparatus, upstream of the sensor assembly;
- wherein the reference assembly includes a keying electrode whose resistance is set to a predetermined magnitude indicating the type of sensor electrodes present in the sensor electrode assembly.

* * * * *